(12) United States Patent
Roh et al.

(10) Patent No.: US 9,464,037 B2
(45) Date of Patent: Oct. 11, 2016

(54) STYRENATED PHENOL COMPOUND AND METHOD OF PREPARING THE SAME

(71) Applicant: Korea Kumho Petrochemical Co., Ltd, Seoul (KR)

(72) Inventors: Kee Yoon Roh, Daejeon (KR); Jung Hee Jang, Daejeon (KR); Je Young Park, Busan (KR); Jin Eok Kim, Daejeon (KR)

(73) Assignee: KOREA KUMHO PETROCHEMICAL CO., LTD, Seoul (KR)

( * ) Notice: Subject to any disclaimer, the term of this patent is extended or adjusted under 35 U.S.C. 154(b) by 0 days.

(21) Appl. No.: 14/779,212

(22) PCT Filed: Sep. 17, 2014

(86) PCT No.: PCT/KR2014/008629
§ 371 (c)(1),
(2) Date: Sep. 22, 2015

(87) PCT Pub. No.: WO2015/046797
PCT Pub. Date: Apr. 2, 2015

(65) Prior Publication Data
US 2016/0046562 A1   Feb. 18, 2016

(30) Foreign Application Priority Data

Sep. 26, 2013   (KR) .................. 10-2013-0114708

(51) Int. Cl.
| | | |
|---|---|---|
| C07C 239/22 | (2006.01) | |
| C07C 37/00 | (2006.01) | |
| C07C 39/15 | (2006.01) | |
| C07C 239/10 | (2006.01) | |
| C08G 59/00 | (2006.01) | |
| C09D 5/44 | (2006.01) | |
| C08K 5/32 | (2006.01) | |
| C09D 163/00 | (2006.01) | |

(52) U.S. Cl.
CPC ............. *C07C 239/22* (2013.01); *C07C 37/00* (2013.01); *C07C 39/15* (2013.01); *C07C 239/10* (2013.01); *C08G 59/00* (2013.01); *C08K 5/32* (2013.01); *C09D 5/4438* (2013.01); *C09D 163/00* (2013.01)

(58) Field of Classification Search
None
See application file for complete search history.

(56) References Cited

U.S. PATENT DOCUMENTS

| | | |
|---|---|---|
| 2,326,782 A | 8/1943 | Jacobus et al. |
| 7,902,280 B2 | 3/2011 | Gelbin et al. |
| 8,193,260 B2 | 6/2012 | Gelbin et al. |

FOREIGN PATENT DOCUMENTS

| | | |
|---|---|---|
| CN | 102267876 A | 12/2011 |
| CN | 102549041 A | 7/2012 |
| GB | 2313782 A | 10/1997 |
| JP | 2797123 B2 | 9/1998 |
| KR | 10-2010-0029120 A | 3/2010 |
| KR | 10-2011-0070081 A | 6/2011 |
| KR | 10-2012-0065836 A | 6/2012 |

OTHER PUBLICATIONS

European Search Report in European Application No. 14186108.8, Jan. 13, 2015.
Office Action dated Jul. 8, 2015 in Taiwanese Application No. 103133247.
G. SH Mamedova P et al, "Optimization of Phenol ortho-Alkylation with Styrene", Petroleum Chemistry, vol. 47, No. 1, Feb. 1, 2007, pp. 55-60.
International Search Report in International Application No. PCT/KR2014/008629, filed Sep. 17, 2014.

*Primary Examiner* — Sudhakar Katakam
*Assistant Examiner* — Jennifer C Sawyer
(74) *Attorney, Agent, or Firm* — Saliwanchik, Lloyd & Eisenschenk

(57) ABSTRACT

Provided is a styrenated phenol compound represented by Formula 1 in which styrenated phenol and hydroxylamine bind to each other:

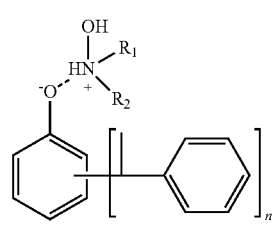

[Formula 1]

In Formula 1, n is one of integers of 1 to 3, and $R_1$ and $R_2$ are each hydrogen or one of C1 to C4 alkyl groups. The styrenated phenol compound may maintain curing stimulation property and plasticity, and prevent discoloration when being mixed with a curing agent for an epoxy paint, thereby enhancing exterior quality and storage stability of a product.

13 Claims, 1 Drawing Sheet

STYRENATED PHENOL COMPOUND AND METHOD OF PREPARING THE SAME

CROSS-REFERENCE TO RELATED APPLICATION

This application is the U.S. national stage application of International Patent Application No. PCT/KR2014/008629, filed Sep. 17, 2014, which claims priority to Korean Application No. 10-2013-0114708, filed Sep. 26, 2013, the disclosures of each of which are incorporated herein by reference in their entirety.

TECHNICAL FIELD

The present invention relates to a styrenated phenol compound and a method of preparing the same, and more particularly, to a styrenated phenol compound in which hydroxylamine binds to styrenated phenol and a method of preparing the same. This application claims priority to and the benefit of Korean Patent Application No. 10-2013-0114708, filed on 26 Sep. 2013, the disclosure of which is incorporated herein by reference in its entirety.

BACKGROUND ART

To provide plasticity to a conventional curing agent composition of an epoxy paint and stimulate curing, alkyl phenol, particularly, nonyl phenol or a styrenated phenol compound has been used.

The alkyl phenol has an anionic molecular structure by dehydrogenating a hydroxyl hydrogen atom of phenol due to basicity of a mixed curing agent, and the generated anions have a quinone-type structure due to resonance in a molecule, resulting in changing a color to yellow or red.

According to a basicity level of the used curing agent, a degree of the discoloration is determined by a rate of being transformed into the quinone-type. When a tertiary amine curing agent having a strong basicity is used, discoloration is rapidly performed, and when a primary amine curing agent is used, discoloration may be a bit delayed, but may not be prevented.

Since the discoloration may deteriorate an exterior quality and storage stability of a product, necessity for a colorless curing agent composition may be increased, and particularly, demands for a product that can be applied to a transparent flooring material are greatly increased. However, a conventional alkyl phenol-type compound is limited to use due to chemical toxicity, and the styrenated phenol compound may also be discolored when being mixed with a curing agent.

DISCLOSURE OF THE INVENTION

Technical Problem

The present invention is provided to solve conventional technical problems, and therefore it is directed to providing a styrenated phenol compound which can maintain a curing stimulation ability and plasticity and prevent discoloration when being mixed with a curing agent to enhance exterior quality and storage stability of a product and a method of preparing the same.

Technical Solution

One aspect of the present invention provides a styrenated phenol compound represented by Formula 1 by binding styrenated phenol and hydroxylamine.

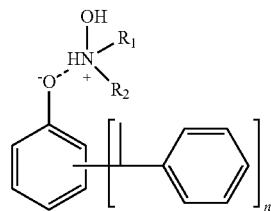

[Formula 1]

In Formula 1, n is one of integers of 1 to 3, and $R_1$ and $R_2$ are each hydrogen or one of C1 to C4 alkyl groups.

In one embodiment of the present invention, the styrenated phenol may include mono-styrenated phenol, di-styrenated phenol, and tri-styrenated phenol, and a content of the mono-styrenated phenol may be 50 wt % or more based on the total weight of the styrenated phenol.

In one embodiment of the present invention, the hydroxylamine may be one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine.

In one embodiment of the present invention, a content of the hydroxylamine may be 0.1 to 15 wt % based on the total weight of the styrenated phenol compound.

Another aspect of the present invention provides a curing agent composition for a paint, which includes a main material part of a curing agent; and a styrenated phenol compound represented by Formula 1 in which styrenated phenol and hydroxylamine bind to each other.

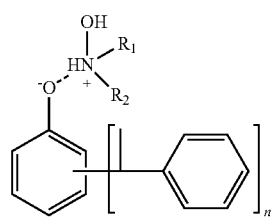

[Formula 1]

In Formula 1, n is one of integers of 1 to 3, and $R_1$ and $R_2$ are each hydrogen or one of C1 to C4 alkyl groups.

In one exemplary embodiment of the present invention, the styrenated phenol may include mono-styrenated phenol, di-styrenated phenol, and tri-styrenated phenol, and a content of the mono-styrenated phenol may be 50 wt % or more based on the total weight of the styrenated phenol.

In one exemplary embodiment of the present invention, the hydroxylamine may be one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine.

In one exemplary embodiment of the present invention, a content of the hydroxylamine may be 0.1 to 15 wt % based on the total weight of the styrenated phenol compound.

In one exemplary embodiment of the present invention, contents of the main material part of a curing agent and the styrenated phenol compound may each be 70 to 90 wt %, and 10 to 30 wt % based on the total weight of the curing agent composition.

Still another aspect of the present invention provides a method of preparing a styrenated phenol compound, which includes synthesizing styrenated phenol by alkylation of phenol and styrene; and preparing a compound represented by Formula 1 by adding hydroxylamine to the styrenated phenol.

[Formula 1]

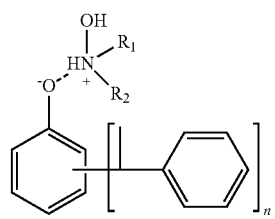

In Formula 1, n is one of the integers of 1 to 3, and $R_1$ and $R_2$ are each hydrogen or one of C1 to C4 alkyl groups.

In one exemplary embodiment of the present invention, the styrenated phenol may include mono-styrenated phenol, di-styrenated phenol, and tri-styrenated phenol, and a content of the mono-styrenated phenol may be 50 wt % or more based on the total weight of the styrenated phenol.

In one exemplary embodiment of the present invention, the hydroxylamine may be one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine.

In one exemplary embodiment of the present invention, a content of the hydroxylamine may be 0.1 to 15 wt % based on the total weight of the styrenated phenol compound.

Advantageous Effects

The styrenated phenol compound prepared by adding hydroxylamine may maintain curing stimulation ability and plasticity of a conventional styrenated phenol compound, and prevent discoloration when being mixed with a curing agent, thereby enhancing exterior quality and storage stability of a product.

Effects of the present invention are not limited to the above-described effects, and it should be understood that the effects include every effect that can be deduced from the configuration of the present invention disclosed in the detailed description or claims of the present invention.

MODE OF THE INVENTION

Figure 1:
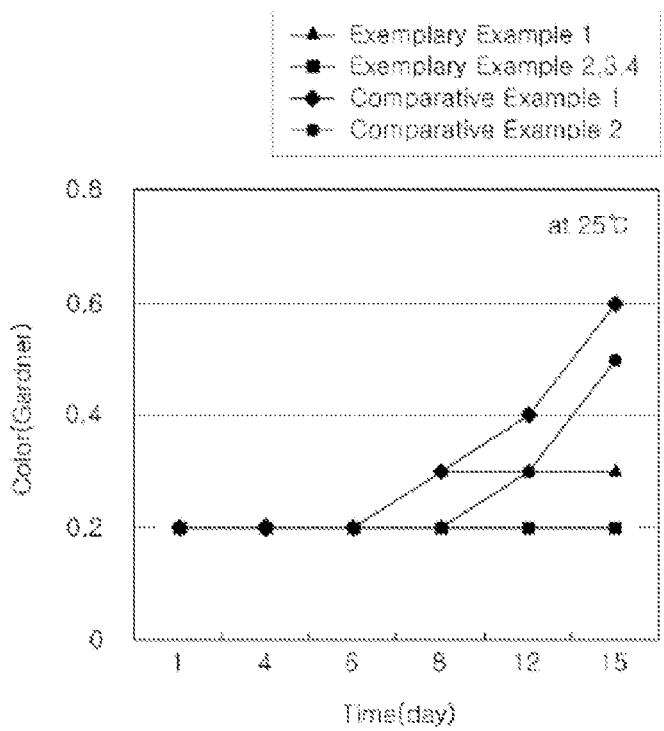
FIG. 1 shows a graph showing a result of a room temperature (25° C.) discoloration test for a curing agent composition to which a styrenated phenol compound is mixed according to time according to an exemplary embodiment.

Hereinafter, the present invention will be described with reference to the accompanying drawings. However, the present invention may be implemented in various forms, and therefore is not limited to the following embodiments.

In the specification, when a part "includes" another component, it means that a third component may be further included without excluding the third component unless there are particularly opposite descriptions.

Hereinafter, embodiments of the present invention will be described in detail with reference to the accompanying drawings.

Styrenated Phenol Compound

According to an aspect of the present invention, a styrenated phenol compound represented by Formula 1 in which styrenated phenol and hydroxylamine bind to each other is provided.

[Formula 1]

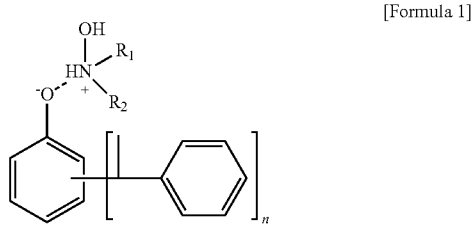

In Formula 1, n is one of the integers of 1 to 3, and $R_1$ and $R_2$ are each hydrogen or one of C1 to C4 alkyl groups.

In one exemplary embodiment of the present invention, the styrenated phenol may include mono-styrenated phenol, di-styrenated phenol, and tri-styrenated phenol, and a content of the mono-styrenated phenol may be 50 wt % or more based on the total weight of the styrenated phenol.

When phenol and styrene are alkylated in the presence of an acid catalyst at 100 to 150° C., mono-styrenated phenol (MSP) in which one styrene binds to a benzene ring of the phenol, di-styrenated phenol (DSP) in which two styrenes are bound, and a tri-styrenated phenol (TSP) compound in which three styrenes are bound may be produced, and a ratio of each product may be determined by an equivalent ratio of the phenol to the styrene, which are reaction materials, a type of the catalyst, or a reaction temperature.

A content of the MSP of the styrenated phenols may be 50 wt % or more, preferably, 50 to 80 wt % based on the total weight of the styrenated phenol.

When the MSP content is 50 wt % or more, a viscosity is decreased, thereby providing plasticity when being mixed with a curing agent, workability may be enhanced, and a hydroxyl value (OH value) may be maintained at a similar level to that of conventional nonyl phenol (240~250), thereby stimulating a curing reaction.

When the hydroxylamine is added to the styrenated phenol, a nitrogen atom of the hydroxylamine may bind to a hydroxyl hydrogen atom of the styrenated phenol, thereby forming a styrenated phenol compound, specifically, a styrenated phenol adduct.

In the curing agent composition prepared by mixing the styrenated phenol adduct with a curing agent, a hydroxyl hydrogen atom of the hydroxylamine, instead of the hydroxyl hydrogen atom of the styrenated phenol may be dehydrogenated, and therefore, a hydroxyl group of the styrenated phenol remains, thereby preventing discoloration of the curing agent composition.

A discoloration preventing mechanism caused by the styrenated phenol compound is shown in Reaction Scheme 1.

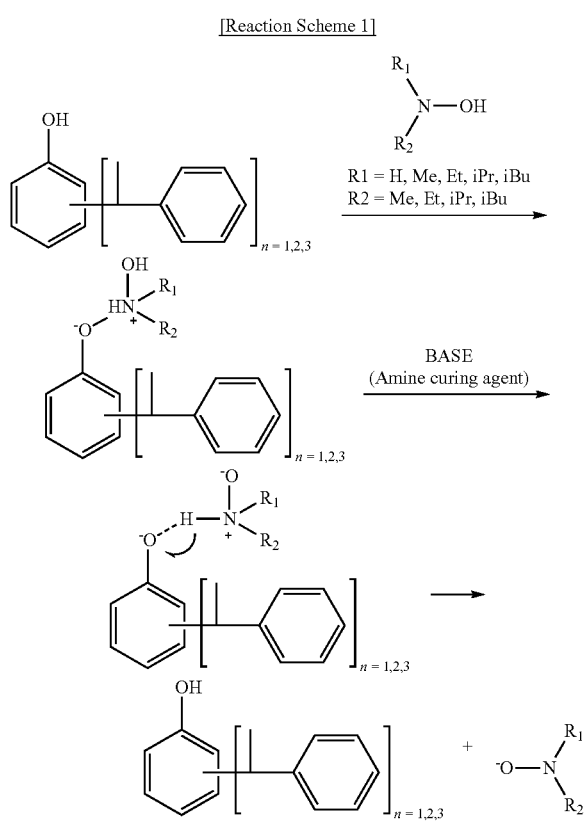

[Reaction Scheme 1]

In one exemplary embodiment of the present invention, the hydroxylamine may be one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine, and preferably, di-ethylhydroxylamine.

In one exemplary embodiment of the present invention, a content of the hydroxylamine may be 0.1 to 15 wt % based on the total weight of the styrenated phenol compound, preferably, 0.1 to 10 wt %, and more preferably, 0.1 to 3 wt %.

When the content of the hydroxylamine is less than 0.1 wt %, a required discoloration preventing function may not be provided, and when the content of the hydroxylamine is more than 15 wt %, hydroxylamines not binding to the styrenated phenol may remain, and therefore reaction efficiency and storage stability may be degraded.

Curing Agent Composition Including Styrenated Phenol Compound

According to another aspect of the present invention, a curing agent composition for a paint is provided, which includes a curing agent main material part; and a styrenated phenol compound represented by Formula 1 in which styrenated phenol binds to hydroxylamine.

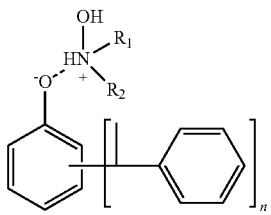

[Formula 1]

In Formula 1, n is one of the integers of 1 to 3, and $R_1$ and $R_2$ are each hydrogen or one of C1 to C4 alkyl groups.

The curing agent main material part may be, but is not limited to, at least one selected from the group consisting of amine-based curing agents such as aliphatic and alicyclic polyamine, aromatic polyamine, and polyamide polyamine; phenol-based curing agents such as a phenol novolac resin, a cresol novolac resin, and a biphenyl-containing phenyl novolac resin; and dicyan diamides, which may be used alone or in combination thereof.

In one exemplary embodiment of the present invention, the styrenated phenol may include mono-styrenated phenol, di-styrenated phenol, and tri-styrenated phenol, and a content of the mono-styrenated phenol may be 50 wt % or more based on the total weight of the styrenated phenol.

In one exemplary embodiment of the present invention, the hydroxylamine may be one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine, and preferably, di-ethylhydroxylamine.

In one exemplary embodiment of the present invention, a content of the hydroxylamine may be 0.1 to 15 wt %, preferably, 0.1 to 10 wt %, and more preferably, 0.1 to 3 wt % based on the total weight of the styrenated phenol compound.

The type and content of the hydroxylamine are the same as the description of the styrenated phenol compound.

In one exemplary embodiment of the present invention, contents of the curing agent main material part and the styrenated phenol compound may be 70 to 90 wt %, and 10 to 30 wt % based on the total weight of the curing agent composition, respectively.

Based on the total weight of the curing agent composition, when the content of the styrenated phenol is less than 10 wt %, plasticity and miscibility may not be provided to the paint or the curing agent main material part at a required level or higher, and when the content of the styrenated phenol is more than 30 wt %, flowability of the paint is excessively increased, and therefore, exterior quality and storage stability of a final product may be degraded.

Method of Preparing Styrenated Phenol Compound

According to still another aspect of the present invention, a method of preparing a styrenated phenol compound is provided, which includes, synthesizing styrenated phenol by alkylation of phenol and styrene; and preparing a compound represented by Formula 1 by adding hydroxylamine to the styrenated phenol.

[Formula 1]

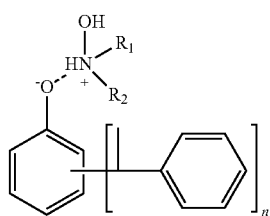

In Formula 1, n is one of the integers of 1 to 3, and $R_1$ and $R_2$ are each hydrogen or one of C1 to C4 alkyl groups.

In one exemplary embodiment of the present invention, the styrenated phenol may include mono-styrenated phenol, di-styrenated phenol, and tri-styrenated phenol, and a content of the mono-styrenated phenol may be 50 wt % or more based on the total weight of the styrenated phenol.

In the step of synthesizing the styrenated phenol, the styrenated phenol may be synthesized by performing the alkylation of the phenol and the styrene in the presence of a phosphoric acid ($H_3PO_4$) catalyst, and adding a sulfuric acid ($H_2SO_4$) or magnesium sulfate ($MgSO_4$) catalyst to terminate the alkylation.

As an initial reaction catalyst to prepare the styrenated phenol, a phosphoric acid ($H_3PO_4$) catalyst may be used. The phosphoric acid catalyst is larger and has a lower activity than a sulfuric acid catalyst in terms of its molecular structure, and thus has a relatively higher reaction temperature.

However, since the phosphoric acid catalyst has a lower reaction activity but higher selectivity than the sulfuric acid catalyst, a composition ratio of the styrenated phenol to be produced may be easily controlled, and specifically, the MSP content in which one styrene is substituted may be controlled to 50 wt % or more, and preferably 60 wt % or more based on the total weight. In addition, the phosphoric acid catalyst has excellent product selectivity since styrene may be substituted at a para position, which is a position of the fourth carbon of the phenol in a higher ratio than the sulfuric acid catalyst.

Meanwhile, when the alkylation is performed only with the phosphoric acid catalyst, unreacted phenols and styrenes may remain in the termination of the reaction. To remove such unreacted remaining materials, at the end point in which dropping of a reactant, styrene, ends, a sulfuric acid ($H_2SO_4$) or magnesium sulfate ($MgSO_4$) catalyst may be used.

An amount of the sulfuric acid or magnesium sulfate catalyst used may be 2 to 10 wt % based on a weight of the phosphoric acid catalyst. When the amount of the sulfuric acid or magnesium sulfate catalyst used is less than 2 wt %, a remainder removing effect may be insignificant, and when the amount of the sulfuric acid or magnesium sulfate catalyst used is more than 10 wt %, it is difficult to separate or recover a product.

After the alkylation, at least one aqueous solution selected from sodium carbonate ($Na_2CO_3$), potassium carbonate ($K_2CO_3$), sodium hydroxide (NaOH), and potassium hydroxide (KOH) may be added to neutralize the alkylation product, and a generated neutralized salt may be removed using a filtration filter, thereby recovering styrenated phenol.

A styrenated phenol compound may be prepared by adding hydroxylamine to the styrenated phenol, and specifically, in the step of preparing a styrenated phenol adduct, a nitrogen atom of the added hydroxylamine may provide an electron pair to a hydroxyl hydrogen atom of the styrenated phenol and thus bind to each other.

In one exemplary embodiment of the present invention, the hydroxylamine may be one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine, and preferably, di-ethylhydroxylamine.

In one exemplary embodiment of the present invention, the content of the hydroxylamine may be 0.1 to 15 wt %, preferably 0.1 to 10 wt %, and more preferably, 0.1 to 3 wt % based on the total weight of the styrenated phenol compound.

The type and content of the hydroxylamine are the same as described for the styrenated phenol compound.

Hereinafter, Examples of the present invention will be described in detail.

Examples 1 to 4

Preparation of Styrenated Phenol Compound and Curing Agent Composition for Epoxy Paint 300 g of phenol and a phosphoric acid ($H_3PO_4$) catalyst (1.876 g, 0.006 eq) were put into a reaction vessel and heated at 140° C., and styrene (381.6 g, 1.15 eq) was dropped for 120 minutes. As the styrene was dropped, a reaction temperature was increased from 140° C. to 170° C. After the dropping of the styrene, the resulting product was further reacted at the same reaction temperature for 1 hour. To remove non-reacted materials, the reaction temperature was decreased to 110° C. and a sulfuric acid ($H_2SO_4$) catalyst (0.05 g, 2 to 10 wt % with respect to the phosphoric acid catalyst) was added to the reactant. As the sulfuric acid was added, the reaction temperature was increased to 125° C., and the reaction was further performed for 30 minutes. The temperature of the reactant was decreased to 80° C., and thereto a sodium carbonate aqueous solution was added in the same equivalent ratio as the sulfuric acid catalyst to neutralize for 30 minutes. A neutralized salt generated above was removed using vacuum evaporation and a filtration filter, thereby yielding styrenated phenol (reaction conversion rate: 97%, purity: 97% or more). As the result of gas chromatography (GC) analysis of the yielded styrenated phenol, it was confirmed that the content of MSP was 67 wt % based on the total weight of the styrenated phenol. The yielded styrenated phenol and di-ethylhydroxylamine were mixed in a weight ratio of 97 to 99 wt %:1 to 3 wt %, respectively, thereby preparing a styrenated phenol compound (plasticizer).

Afterward, the styrenated phenol compound and a known curing agent for an epoxy paint (Jeffamine 230) were added to a magnetic stirrer in a weight ratio of 15 to 30 wt %:70 to 85 wt %, and stirred at room temperature for 10 minutes, thereby preparing a curing agent composition for an epoxy paint.

Comparative Examples 1 and 2

Preparation of Curing Agent Composition for Epoxy Paint Containing Nonyl Phenol Compound A curing agent composition for an epoxy paint was prepared by adding nonyl phenol and a known curing agent for an epoxy paint (Jeffamine 230) to a magnetic stirrer in a weight ratio of 15 to 30 wt %:70 to 85 wt % and stirring the mixture at a room temperature for 10 minutes.

Mixing ratios between components of curing agent compositions for an epoxy paint according to Examples 1 to 4 and Comparative Examples 1 and 2 are shown in Table 1.

TABLE 1

| Category | Epoxy curing agent (A) | Plasticizer (B) Styrenated phenol | Plasticizer (B) Di-ethyl-hydroxylamine | Mixing ratio (A:B, wt %) |
|---|---|---|---|---|
| Example 1 | Jeffamine 230 | 99 wt % | 1 wt % | 85:15 |
| Example 2 | | 98 wt % | 2 wt % | 85:15 |
| Example 3 | | 97 wt % | 3 wt % | 85:15 |
| Example 4 | | 97 wt % | 3 wt % | 70:30 |
| Comparative Example 1 | Jeffamine 230 | Nonyl phenol | | 70:30 |
| Comparative Example 2 | | Nonyl phenol | | 85:15 |

Experimental Example 1

Room Temperature (25° C.) Discoloration Test

For the curing agent compositions for an epoxy paint according to Examples 1 to 4 and Comparative Examples 1 and 2, discoloration according to time at room temperature (25° C.) was detected using an OME-2000 color meter.

Experimental Example 2

High Temperature (60° C.) Discoloration Test

Discoloration at a high temperature compared to the room temperature is a main factor having an effect on storage stability. For the curing agent compositions for an epoxy paint according to Examples 1 to 4 and Comparative Examples 1 and 2, discoloration according to time at a high temperature (60° C.) was detected using an OME-2000 color meter.

Figure 2:
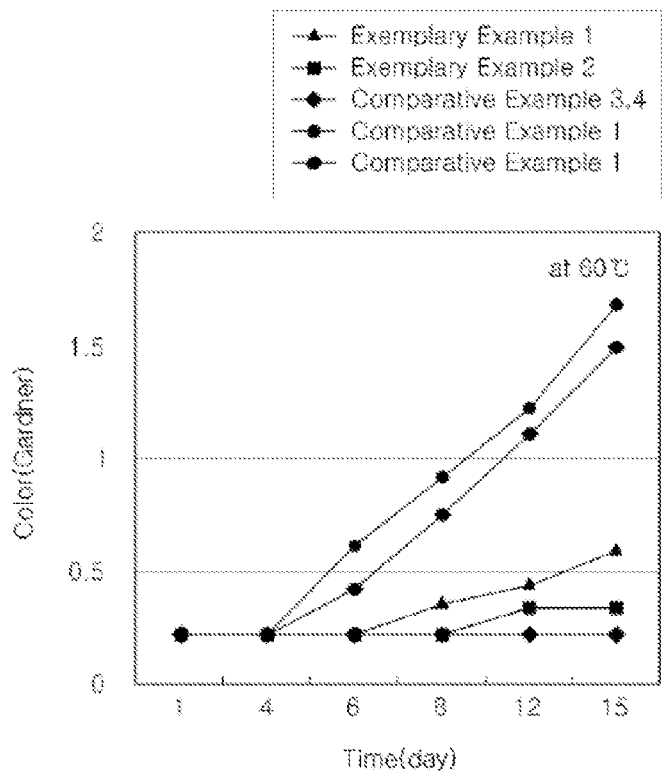
FIG. 2 is a graph showing a result of a high temperature (60° C.) discoloration test for a curing agent composition to which a styrenated phenol compound is mixed according to time according to an exemplary embodiment.

Results of the discoloration tests according to Experimental Examples 1 and 2 are shown in Table 2, and FIGS. 1 and 2.

According to the results of the room temperature (25° C.) and high temperature (60° C.) discoloration tests, it was shown that as the content of di-ethylhydroxylamine was increased within a range from 1 to 3 wt % based on the total weight of the styrenated phenol compound, an effect of preventing discoloration was enhanced, and excellent storage stability was exhibited (refer to Examples 1 to 3).

In addition, comparing the result of the room temperature (25° C.) discoloration test and the result of the high temperature (60° C.) discoloration test, the curing agent compositions for an epoxy paint of Examples 1 to 4 showed considerable decreases in discoloration range according to temperature variation, comparing to those of Comparative Examples 1 and 2.

According to Experimental Examples 1 and 2, it was confirmed that the hydroxylamine-added styrenated phenol compound had an excellent effect of preventing discoloration to the curing agent composition for an epoxy paint, compared to the nonyl phenol compound, and therefore exterior quality and storage stability of the product were enhanced.

The above descriptions of the present invention are provided to explain the present invention as examples, and those of ordinary skill in the art should understand that the present invention can be easily modified in other specific types without changing the technical ideas or essential characteristics. Therefore, it should be understood that all of the embodiments described above are merely provided to explain, but not to limit the present invention. For example, components that are described in a single type may be dispersed, and the components that were explained to be dispersed may be bound to each other.

While the invention has been shown and described with reference to certain exemplary embodiments thereof, it will be understood by those skilled in the art that various modifications in form and details may be made therein without departing from the spirit and scope of the invention as defined by the appended claims.

The invention claimed is:

1. A styrenated phenol compound having the structure of Formula 1, comprising:
   styrenated phenol; and
   hydroxylamine, which binds to the styrenated phenol:

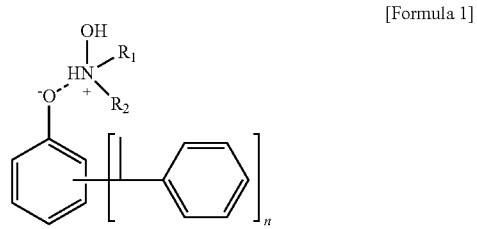

[Formula 1]

TABLE 2

| Category | Room temperature (25) discoloration test | | | | | | High temperature (60) discoloration test | | | | | |
|---|---|---|---|---|---|---|---|---|---|---|---|---|
| | 1 day | 4 day | 6 day | 8 day | 12 day | 15 day | 1 day | 4 day | 6 day | 8 day | 12 day | 15 day |
| Example 1 | 0.2 | 0.2 | 0.2 | 0.2 | 0.3 | 0.3 | 0.2 | 0.2 | 0.2 | 0.3 | 0.4 | 0.6 |
| Example 2 | 0.2 | 0.2 | 0.2 | 0.2 | 0.2 | 0.2 | 0.2 | 0.2 | 0.2 | 0.2 | 0.3 | 0.3 |
| Example 3 | 0.2 | 0.2 | 0.2 | 0.2 | 0.2 | 0.2 | 0.2 | 0.2 | 0.2 | 0.2 | 0.2 | 0.2 |
| Example 4 | 0.2 | 0.2 | 0.2 | 0.2 | 0.2 | 0.2 | 0.2 | 0.2 | 0.2 | 0.2 | 0.2 | 0.2 |
| Comparative Example 1 | 0.2 | 0.2 | 0.2 | 0.3 | 0.4 | 0.6 | 0.2 | 0.2 | 0.6 | 0.9 | 1.2 | 1.7 |
| Comparative Example 2 | 0.2 | 0.2 | 0.2 | 0.3 | 0.3 | 0.5 | 0.2 | 0.2 | 0.4 | 0.7 | 1.1 | 1.5 | where n is one of integers of 1 to 3, and $R_1$ and $R_2$ are each hydrogen or one of C1 to C4 alkyl groups.

2. The compound according to claim 1, wherein the styrenated phenol includes mono-styrenated phenol, di-styrenated phenol, and tri-styrenated phenol, and a content of the mono-styrenated phenol is 50 wt % or more based on the total weight of the styrenated phenol.

3. The compound according to claim 1, wherein the hydroxylamine is one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine.

4. The compound according to claim 1, wherein a content of the hydroxylamine is 0.1 to 15 wt % based on the total weight of the styrenated phenol compound.

5. A curing agent composition for a paint, comprising:
a main material part of a curing agent; and
a styrenated phenol compound having the structure of Formula 1 in which styrenated phenol and hydroxylamine bind to each other:

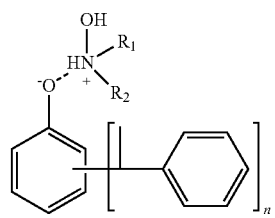

[Formula 1]

where n is one of integers of 1 to 3, and $R_1$ and $R_2$ are each hydrogen or one of C1 to C4 alkyl groups.

6. The composition according to claim 5, wherein the styrenated phenol includes mono-styrenated phenol, di-styrenated phenol, and tri-styrenated phenol, and a content of the mono-styrenated phenol is 50 wt % or more based on the total weight of the styrenated phenol.

7. The composition according to claim 5, wherein the hydroxylamine is one selected from the group consisting of mono-methylhydroxylamine, di-methylhydroxylamine, mono-ethylhydroxylamine, di-ethylhydroxylamine, mono-propylhydroxylamine, di-isopropylhydroxylamine, and di-isopropylhydroxylamine.

8. The composition according to claim 5, wherein a content of the hydroxylamine is 0.1 to 15 wt % based on the total weight of the styrenated phenol compound.

9. The composition according to claim 5, wherein contents of the main material part of a curing agent and the styrenated phenol compound are 70 to 90 wt % and 10 to 30 wt % based on the total weight of the curing agent composition, respectively.

10. A method of preparing a styrenated phenol compound, comprising:
synthesizing styrenated phenol by alkylation of phenol and styrene; and
preparing a compound of Formula 1 by adding hydroxylamine to the styrenated phenol:

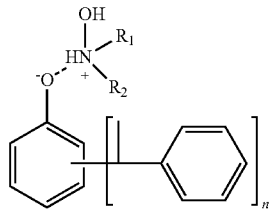

[Formula 1]

where n is one of integers of 1 to 3, and $R_1$ and $R_2$ are each hydrogen or one of C1 to C4 alkyl groups.

11. The method according to claim 10, wherein the styrenated phenol includes mono-styrenated phenol, di-styrenated phenol, and tri-styrenated phenol, and a content of the mono-styrenated phenol is 50 wt % or more based on the total weight of the styrenated phenol.

12. The method according to claim 10, wherein the hydroxylamine is one selected from the group consisting of mono-methylhydroxylamine, di-methylhydroxylamine, mono-ethylhydroxylamine, di-ethylhydroxylamine, mono-propylhydroxylamine, di-propylhydroxylamine, mono-butylhydroxylamine, di-butylhydroxylamine, isopropylhydroxylamine, and di-isopropylhydroxylamine.

13. The method according to claim 10, wherein a content of the hydroxylamine is 0.1 to 15 wt % based on the total weight of the styrenated phenol compound.

* * * * *